United States Patent
Loo et al.

(10) Patent No.: US 9,381,163 B2
(45) Date of Patent: Jul. 5, 2016

(54) FLOATING CAPSULES ENCAPSULATING PARTICLES LOADED WITH ONE OR MORE DRUGS

(71) Applicant: NANYANG TECHNOLOGICAL UNIVERSITY, Singapore (SG)

(72) Inventors: Say Chye Joachim Loo, Singapore (SG); Wei Li Lee, Singapore (SG); Peixin Wee, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/415,485

(22) PCT Filed: Jul. 8, 2013

(86) PCT No.: PCT/SG2013/000282
§ 371 (c)(1),
(2) Date: Jan. 16, 2015

(87) PCT Pub. No.: WO2014/027956
PCT Pub. Date: Feb. 20, 2014

(65) Prior Publication Data
US 2015/0164815 A1    Jun. 18, 2015

Related U.S. Application Data

(60) Provisional application No. 61/683,955, filed on Aug. 16, 2012.

(51) Int. Cl.
| | | |
|---|---|---|
| *A61K 9/48* | (2006.01) | |
| *A61K 9/66* | (2006.01) | |
| *A61K 31/235* | (2006.01) | |
| *A61K 31/155* | (2006.01) | |
| *A61K 9/50* | (2006.01) | |
| *A61K 9/00* | (2006.01) | |
| *A61K 45/06* | (2006.01) | |
| *A61K 31/138* | (2006.01) | |
| *A61K 31/216* | (2006.01) | |

(52) U.S. Cl.
CPC .............. *A61K 9/5031* (2013.01); *A61K 9/0065* (2013.01); *A61K 31/138* (2013.01); *A61K 31/155* (2013.01); *A61K 31/216* (2013.01); *A61K 45/06* (2013.01)

(58) Field of Classification Search
None
See application file for complete search history.

(56) References Cited

U.S. PATENT DOCUMENTS 6,207,197 B1    3/2001    Illum et al.

OTHER PUBLICATIONS

Chandel et al., "Floating drug delivery systems: A better approach," *International Current Pharmaceutical Journal* 1(5):110-118, 2012.

*Primary Examiner* — Jeffrey T Palenik
(74) *Attorney, Agent, or Firm* — Seed IP Law Group PLLC

(57) ABSTRACT

The invention relates to capsules encapsulating particles loaded with one or more drugs, and in particular, to such capsules that are able to float. The capsules may be used for drug delivery in the gastrointestinal tract. Methods for forming the capsules are also disclosed, and in particular, double emulsion methods are used in forming the capsules.

20 Claims, 11 Drawing Sheets

FLOATING CAPSULES ENCAPSULATING PARTICLES LOADED WITH ONE OR MORE DRUGS

CROSS-REFERENCE TO RELATED APPLICATION

This application claims the benefit of priority of U.S. Provisional Patent Application No. 61/683,955, filed Aug. 16, 2012, the contents of which being hereby incorporated by reference in its entirety for all purposes.

TECHNICAL FIELD

The invention relates to capsules encapsulating particles loaded with one or more drugs, and in particular, to such capsules that are able to float. The capsules may be used for drug delivery in the gastrointestinal tract. Methods for forming the capsules are also disclosed, and in particular, double emulsion methods are used in forming the capsules.

BACKGROUND

Despite tremendous advancement in drug delivery, oral administration still remains the most convenient and preferred means of drug delivery due to its low cost, ease of administration and flexibility in formulation. However, conventional oral dosage forms (e.g. tablets, capsules) have several inherent limitations, including a limited control over drug release rates, lack of complete absorption of oral drugs due to variable and short gastrointestinal (GI) transit time, and high fluctuation in plasma drug levels due to multiple dosing frequency. Dosage forms with a prolonged gastric residence time (GRT) have been used to circumvent some of these problems. Gastro-retentive delivery systems have the potential to improve bioavailability and reduce drug wastage that show preferential solubility, stability or absorption in the stomach or the proximal part of the GI tract.

Several approaches to prolong the GRT have been proposed based on various mechanisms, such as buoyancy (floating drug dosage systems, FDDS), swelling/plug type, high density and mucoadhesion. The constant renewal and high turnover of mucus may reduce the effectiveness of mucoadhesive systems. Unlike the retention of swelling systems and high density systems in the pylorus and the pyloric antrum, respectively, floating systems do not adversely affect the motility of the stomach. As such, FDDS have been extensively studied to retain drug forms in the stomach. With this, various floating systems have thus been developed using different materials (e.g. lipids, hydroxypropyl methylcellulose (HPMC)-based hydrodynamically balanced systems and alginate beads containing gas-generating agents) for controlled delivery of drugs.

While conventional oral drug delivery devices involve monolithic systems whereby only one drug is loaded, basic economics and patient compliance would favor the realization of a single microcapsule that simultaneously entraps and releases multiple drugs in a controlled manner. A single carrier or "tablet" that encapsulates multiple drugs would allow for a reduction in the number of oral tablets to be taken, as well as in the dosing frequency (i.e. pill burden), which in turn may improve patient compliance. Drug-drug interactions can also be avoided if individual drug substances are further protected within particles. Such a technology could potentially be used to treat diseases that require multiple drug combinations, such as HIV, cancer, tuberculosis and lupus. Another therapeutic area whereby floating microcapsules could be explored is for the treatment of chronic gastritis and peptic ulcers.

Though floating single drug dosage forms have already been well-established, there is a dearth of studies demonstrating the encapsulation of particles loaded with different drugs, while maintaining good floatability. It is thus hypothesized that the encapsulation of drug-loaded particles within a larger hollow capsule would provide good buoyancy, along with controlled release of multiple drugs. The addition of oil into the capsule shell can provide this extra buoyancy. The manipulation of capsule/particle parameters, such as shell thickness, particle sizes, and polymer types, can be tuned to control drug release rates.

SUMMARY

The inventors have demonstrated the encapsulation of drug-loaded particles within the hollow cavity or core of a polymer-based capsule. The capsule can be used for sustained release or controlled release in oral drug delivery systems. The capsule can be a floating capsule such that when administered orally, the encapsulated drug-loaded particles can exhibit a longer residence time in the gastric region. Gastric retention systems offer numerous advantages, including improved bioavailability and reduced wastage of drugs that show preferential solubility, stability or absorption in the stomach or the proximal part of the gastrointestinal tract. Such systems could also be advantageous for reduced variability in gastrointestinal transit time and local action in the gastric and proximal intestinal region.

Floating drug delivery systems have been employed to retain the dosage form in the stomach for a prolonged period of time. The nature of this invention allows for the entrapment and sustained release of multiple active ingredients from a single floating capsule, with the intention of reducing the number of tablets that need to be taken orally, which in turn may facilitate ease of handling and administration of drugs.

Thus, in accordance with a first aspect, there is provided a method for forming a floating capsule encapsulating particles (S) loaded with one or more drugs. The method may include suspending the particles (S) in an aqueous phase (W1) to form a S/W1 phase. The method may further include contacting the S/W1 phase with a solution of a polymer (O) in a first organic solvent to form a S/W1/O phase. The method may further include adding a water-immiscible oil with a density lower than water to the S/W1/O phase. The method may further include combining the S/W1/O phase including the water-immiscible oil with a water bath (W2) including a surfactant and a second organic solvent and emulsifying the resulting mixture to form a S/W1/O/W2 phase, and evaporating under reduced pressure the organic solvents in the S/W1/O/W2 phase to obtain the capsule.

According to a second aspect, there is provided a floating capsule formed of a core-shell structure, wherein particles loaded with one or more drugs are encapsulated within the core and the shell is free of the particles. The capsule can be a sustained release or controlled release capsule, and can be used for drug delivery in the gastrointestinal tract.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1:
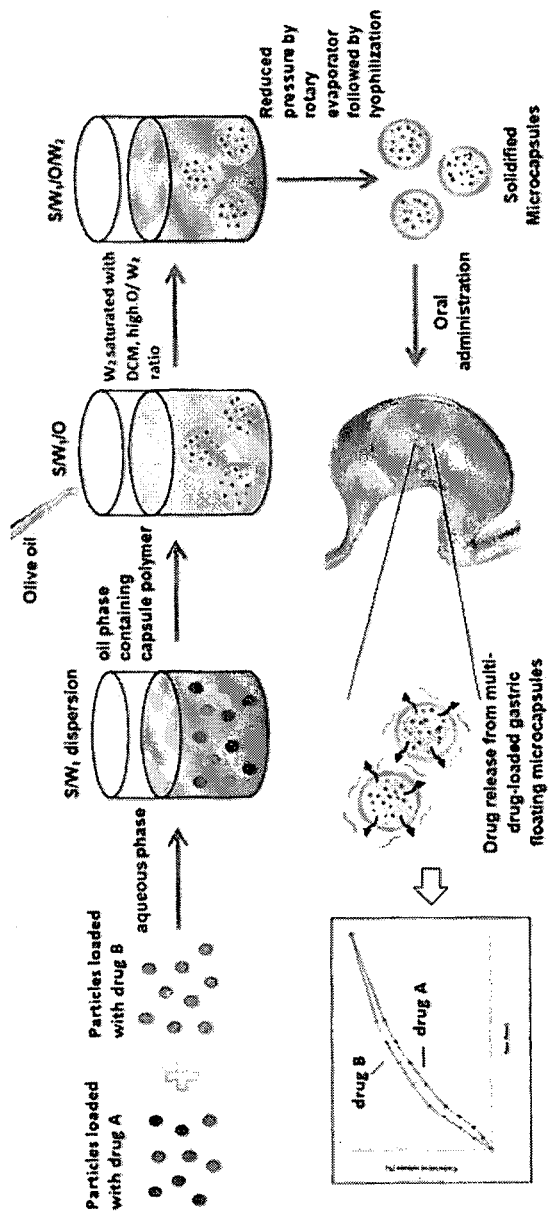
FIG. 1 shows a schematic illustration of the present encapsulation procedure for the preparation of floating microcapsules and the release of multiple drugs within the gastric region.

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

While floating drug delivery systems have already been well-established, there is still minimal study investigating the encapsulation of particles loaded with one or more different drugs within a hollow core of a capsule (may also be termed as a microcapsule, which is used interchangably in the present context), while at the same time provide some degree of floatability of the capsule. The addition of oil into the capsule shell can provide extra buoyancy. Although the inclusion of oil to increase floatability may be known, the addition of the oil to the microcapsule while achieving the ability to load drug-loaded particles together in the microcapsule is not trivial. The addition of oil would change the structure, morphology, encapsulation capability of the microcapsule, and particle localization within the microcapsule. This therefore requires the redesign of the fabrication or formulation process.

Advantageously, the present disclosure relates not only about encapsulating particles loaded with different drug types, but also the ability to provide sustained or controlled release of multiple drugs from a single floating capsule. Further, with the presently disclosed methods, the inventors are able to:

1. Produce particles carrying a wide range of drugs and exhibiting unique release properties based on the polymer types, molecular weight, and drug loading, for example.

2. Encapsulate a population of particles within a single polymeric microcapsule through a one-step packaging process.

3. Prepare the microcapsule with good buoyancy properties, thus extending gastric residence time.

4. Control the size and shell thickness of the capsule as well as the encapsulated particle sizes.

Achieving the above would provide a versatile and robust approach to release multiple drugs, and yet achieve controlled drug release in the gastric region for a prolonged period of time. To this end, the inventors have devised a modified emulsion solvent evaporation technique to encapsulate smaller drug-loaded particles (nano/micron-sized) within a larger floating microcapsule.

In accordance with one aspect, there is provided a method for forming a floating capsule encapsulating particles (S) loaded with one or more drugs. The method may include suspending the particles (S) in an aqueous phase (W1) to form a S/W1 phase. The method may further include contacting the S/W1 phase with a solution of a polymer (O) in a first organic solvent to form a S/W1/O phase. The method may further include adding a water-immiscible oil with a density lower than water to the S/W1/O phase. The method may further include combining the S/W1/O phase including the water-immiscible oil with a water bath (W2) including a surfactant and a second organic solvent and emulsifying the resulting mixture to form a S/W1/O/W2 phase, and evaporating under reduced pressure the organic solvents in the S/W1/O/W2 phase to obtain the capsule.

As mentioned above, the present method refers to a modified emulsion technique. Emulsification refers to the process of emulsifying in which two immiscible liquids are mixed together (e.g. by shaking, stirring or homogenizing) forming an emulsion. Thus, an emulsion is a disperse system of two or more immiscible liquids. One of the liquids forms a dispersant (also called continuous phase) in which the other phase (also called dispersed phase) is distributed in form of fine droplets. Emulsifying of one liquid in the other results in the formation of small droplets of one liquid dispersed (separated and distributed throughout the space) in the other liquid.

Most emulsions consist of water and oil as immiscible phases. Depending on the composition and ratio of the phases two distribution options exist. In case water "W" is the continuous phase and the oil "O" is the dispersed phase, the result is an "O/W emulsion" whose basic character is determined by the aqueous phase. If oil "O" is the continuous phase and water "W" the dispersed phase, the result is a "W/O emulsion", whose basic character is determined by the oil.

When applying this knowledge to the method of the present invention, it becomes obvious that the method of the present invention uses a S/W/O/W emulsion for the manufacture of capsules of the present invention.

The capsule of the present disclosure generally has a core-shell structure. The capsule may be comprised of a polymeric material. The core of the capsule may be hollow and encapsulates the particles loaded with one or more drugs therein (or simply termed as drug-loaded particles, which is used interchangably in the present context). By "encapsulating" in the present context, it is to be understood that the drug-loaded particles are surrounded by the polymeric shell of the capsule. It is to be further understood that essentially all of the drug-loaded particles are surrounded by the polymeric shell of the capsule and essentially no drug-loaded particles are embedded or trapped in the polymeric shell of the capsule. In other words, the presently disclosed capsule may be formed of a core-shell structure, wherein particles loaded with one or more drugs are encapsulated within the core and the shell is free of the particles. The capsule can be a sustained release or controlled release capsule, and can be used, for example, for drug delivery in the gastrointestinal tract.

In various embodiments, the particles (S) may include one or more types of particles, each type of particle loaded with a different drug or drug combination. For example, the one or more drugs may be selected from the group consisting of ibuprofen (IBU), metoclopramide HCl (MCA) lidocaine, atorvastatin, clopidogrel, enoxaparin, celecoxib, omeprazole, esomeprazole, fexofenadine, quetiapine, metoprolol tartrate, metformin hydrochloride, fenofibrate, budesonide, and a mixture thereof.

A solution of a polymer (O) in a first organic solvent may be formed by dissolving the polymer in the first organic solvent.

In various embodiments, the first organic solvent which is immiscible with water may be selected from the group consisting of dichloromethane (DCM), ethyl acetate (EAc), methyl ethyl ketone (MEK), tetrahydrofuran (THF), chloroform, pentane, benzene, benzyl alcohol, and carbon tetrachloride. For example, the first organic solvent may be DCM.

The polymer solution may be comprised of a biocompatible or biodegradable polymer which is insoluble in water. In various embodiments, the polymer solution (O) may contain a polymer selected from the group consisting of poly(lactide) (PLA), poly(glycolide) (PGA), poly(ε-caprolactone) (PCL), poly(δ-valerolactone), poly(γ-butyrolactone), poly(trimethylene carbonate), polyisopropylacrylamide, poly(hydroxylbutyrate-co-hydroxyvalerate) (PHB or PHBV) and a copolymer or mixture thereof. For example, the polymer solution (O) may contain a copolymer of PLA and PGA, i.e. the polymer may be poly(L,D-lactic-co-glycolic acid) (PLGA).

In certain embodiments, the polymer solution (O) is comprised of PLGA dissolved in the first organic solvent, such as DCM.

The S/W1 phase is contacted with the polymer solution (O) to form a S/W1/O phase. The S/W1 phase may, for example, be added to the polymer solution (O). In certain embodiments, the S/W1 phase may be added dropwise to the polymer solution (O).

After forming the S/W1/O phase, a water-immiscible oil with a density lower than water is added to the S/W1/O phase. The water-immiscible oil with a density lower than water is used so as to impart buoyancy to the resultant capsule such that the capsule is able to float in the gastric or intestinal fluid in the GI tract.

The volume ratio of the water-immiscible oil:first organic solvent should be kept as low as possible and yet still able to provide sufficient buoyancy for the resultant capsules. Thus, in various embodiments, the water-immiscible oil is a vegetable oil, preferably added in a vegetable oil:first organic solvent volume ratio of 1% or less, such as 0.9% or less, 0.8% or less, 0.7% or less, 0.6% or less, 0.5% or less, 0.4% or less, 0.3% or less, 0.2% or less, or preferably 0.15%.

The water-immiscible oil may, for example, be olive oil.

In certain embodiments, the water-immiscible oil may be olive oil and the first organic solvent may be DCM, and the volume ratio of vegetable oil:first organic solvent may be about 0.15%.

After forming the S/W1/O phase including the water-immiscible oil, the S/W1/O phase is combined with a water bath (W2) including a surfactant and a second organic solvent and the resulting mixture is emulsified to form a S/W1/O/W2 phase. For example, the S/W1/O phase may be added to the water bath (W2). Alternatively, the water bath (W2) may be added to the S/W1/O phase. The resultant mixture may be emulsified, for example, by using a overhead stirrer. The stirring speed of the stirrer may be manipulated to control the sizes of particles and capsules.

In various embodiments, the second organic solvent which is immiscible with water may be the same or different from the first organic solvent.

In certain embodiments, the second organic solvent may be the same as the first organic solvent and may be selected from the group as defined for the first organic solvent. For example, the first and second organic solvents may be the same and are both DCM.

In various embodiments, the water bath (W2) may contain a saturated amount of the second organic solvent.

The polymer solution:water bath (O/W2) volume ratio should be kept far above the solubility of first organic solvent in water. For example, solubility of DCM in water is 2% v/v. Hence, in various embodiments, the S/W1/O/W2 phase may include a polymer solution:water bath (O/W2) volume ratio of 12% v/v or more, such as 13% v/v or more, 14% v/v or more, 15% v/v or more, 16% v/v or more, 17% v/v or more.

In various embodiments, the surfactant may be selected from the group consisting of polyvinyl alcohol (PVA), sodium dodecyl sulfate (SDS), sodium pentane sulfonate, dehydrocholic acid, glycolithocholic acid ethyl ester, ammonium lauryl sulfate and other alkyl sulfate salts, sodium laureth sulfate, alkyl benzene sulfonate, soaps, fatty acid salts, poloaxamers, alkyl poly(ethylene oxide), diethylene glycol monohexyl ether, copolymers of poly(ethylene oxide) and poly(propylene oxide), hexaethylene glycol monohexadecyl ether, alkyl polyglucosides, digitonin, ethylene glycol monodecyl ether, cocamide MEA, cocamide DEA, cocamide TEA, fatty alcohols, cetyl trimethylammonium bromide (CTAB), dodecylethyldimethylammonium bromide (D12EDMAB), didodecyl ammonium bromide (DMAB), cetylpyridinium chloride (CPC), polyethoxylated tallow amine (POEA), hexadecyltrimethylammonium p-toluenesulfonate, benzalkonium chloride (BAC), benzethonium chloride (BZT), dodecyl betaine, sodium 2,3-dimercaptopropanesulfonate monohydrate, dodecyl dimethylamine oxide, cocamidopropyl betaine, 3-[N,N-dimethyl(3-palmitoylaminopropyl)ammonio]-propanesulfonate, coco ampho glycinate, and mixture thereof. For example, the surfactant may be PVA.

In certain embodiments, the water bath (W2) may include PVA and DCM.

After forming the S/W1/O/W2 emulsion, the organic solvents in the S/W1/O/W2 phase are evaporated to obtain the capsule encapsulating the particles loaded with one or more drugs.

During emulsification, the solvent extraction rate is reduced by increasing the oil-to-water (O/W2) ratio and saturating the continuous aqueous phase with the second organic solvent. This would reduce the probability of agglomeration of the encapsulated particles. Subsequently, during the hardening process to form the capsules, the precipitation rate is accelerated through the use of a rotary evaporator under reduced pressure, and through the addition of extra water or surfactant. As a result, an increased removal rate of the first organic solvent from the emulsion droplets to the external aqueous phase would reduce the time allowed for the adhesion process between the encapsulated particles and inner water/oil interface to take place. This would then give rise to a true encapsulation of particles within the microcapsule, and not having particles embedded in the shell of the microcapsule.

Accordingly, in various embodiments, evaporating the organic solvents may include evaporating the organic solvents under reduced pressure. In certain embodiments, the organic solvents are evaporated using a rotary evaporator under reduced pressure.

In various embodiments, the step of evaporating the organic solvents may further include adding more water or surfactant to the S/W1/O/W2 phase. The surfactant may be selected from the group as defined above.

The thus-formed capsule may be further processed, for example, filtering, rinsing, lyophilizing or storing the capsule.

In summary, the presently optimized emulsion solvent evaporation method allows for the fabrication of floating microcapsule with different drug-loaded particles encapsulated. While conventional floating polymeric release systems often revolve around the use of a single drug formulation, basic economics and patient compliance would favor the realization of a single carrier that can host and release multiple drug entities. The presently disclosed methodology represents a more advanced floating carrier that simultaneously entraps and releases multiple drugs in a controlled manner, which would reduce the dosing frequency and pill burden. Drug-drug interactions can also be avoided in such delivery systems as drug substances are protected by the particles. The present capsules can offer greater versatility in controlling drug release through the manipulation of capsule/particle parameters, such as shell thickness, particle sizes, and polymer types. In the present methods, high compression force and elevated temperature are not necessarily involved, as compared to common methods of producing floating tablets or formulations. Only simple and economical laboratory apparatus, such as an overhead stirrer, rotary evaporator, are required in this fabrication approach, as compared to other existing method where complex and expensive fabrication equipment are required. This fabrication process is therefore highly scalable. In addition, vegetable oil (for extra buoyancy) and particles, hosting a variety of different drugs, can be concurrently loaded into a single hollow microcapsule through a single step. This would aid in improving the process yield and reduce the quality control problems in comparison to the multiple-step process.

In order that the invention may be readily understood and put into practical effect, particular embodiments will now be described by way of the following non-limiting examples.

EXAMPLES

The inventors have devised a modified emulsion solvent evaporation technique to encapsulate smaller drug-loaded particles (nano/micron-sized) within a larger floating microcapsule. In this present technique, high compression forces and elevated temperatures are not required, as compared with other common methods of producing floating tablets. In addition, vegetable oil and particles loaded with a variety of drugs can be concurrently encapsulated into a single microcapsule through a single step, thus improving process yield and quality control.

In the discussion described in following paragraphs, a general fabrication technique in accordance with various embodiments for the preparation of floating microcapsules for drug delivery is described.

The floating microcapsules are prepared using solid/water/oil/water (S/W1/O/W2) emulsion solvent evaporation method, as shown in FIG. 1. Briefly, pre-synthesized drug-loaded particles (either sub-micron or nano-sized) are first suspended in aqueous phase. Subsequently, the particles/water suspension (S/W1) is introduced into a polymer solution (O) to form the S/W1/O phase before adding the vegetable oil (e.g. olive oil). The polymer solution (O) is prepared by dissolving the polymer in a volatile organic solvent (e.g. DCM). The resultant S/W1/O phase is poured into a water bath (W2) containing both a surfactant (e.g. (PVA) and an organic solvent (e.g. DCM), and emulsified to form S/W1/O/W2 emulsion using an overhead stirrer. After which, the hardening of the shell of the capsule is achieved under reduced pressure using a rotary evaporator with an addition of extra surfactant solution. Finally, the microcapsules produced are filtered, rinsed with de-ionized water, lyophilized and stored in a desiccator.

Example 1

In this study, three model drugs (i.e. metoprolol tartrate salt, metformin HCl, fenofibrate) were encapsulated within larger microcapsules. These drug choices would allow this delivery system to be used for the treatment of chronic cardiovascular diseases, i.e. high blood pressure, blood glucose and cholesterol.

Drug-loaded poly(lactide-co-glycolide) (PLGA) particles were formed by oil-in-oil emulsion. Firstly, 0.2 g of PLGA and drug were added to 1 mL of dichloromethane (DCM) and 1 mL of acetonitrile (ACN). Subsequently, the polymer/drug solution was poured into 50 mL of paraffin oil with 0.3% v/v of span 80. The mixture was then subjected to an overhead stirring (800 rpm) for 10 min before being transferred quickly to a rotary evaporator. The particles were then collected by centrifugation, washed with petroleum ether (e.g. heptane), and dried in vacuum oven. The particles were finally reconstituted and suspended in 1 mL of poly(vinyl alcohol) (PVA)-containing water (4 w/v) before centrifugation and decantation.

Figure 2A:
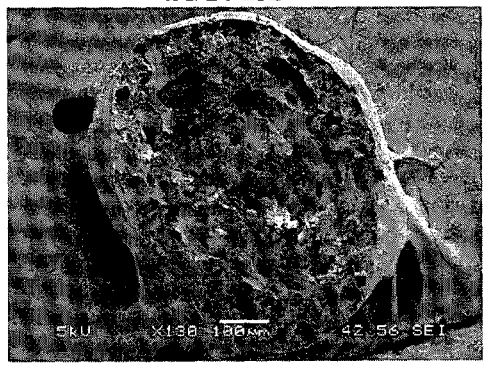
FIG. 2A shows a scanning electron micrograph (SEM) of a cross-sectional view of an entire microcapsule with smaller particles encapsulated within the interspatial regions or cores. (a) Whole microcapsule and (b) close-up view
Figure 2B:
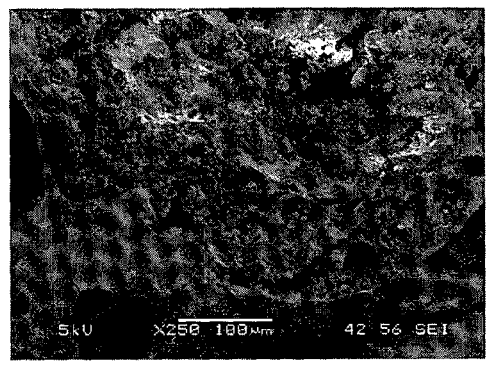
FIG. 2B shows a SEM of a partial, close-up cross-sectional view of a microcapsule with smaller particles encapsulated within the interspatial regions or cores.

For the encapsulation step, 0.3 g of PLGA (5% w/v) was first dissolved in 6 mL of DCM. The pre-synthesized particles were suspended in 1 mL of PVA aqueous solution (0.1% w/v). The particles/water suspension was then introduced dropwise into the PLGA solution followed by the addition of olive oil (0.01 mL) under magnetic stirring. The resultant mixture was added to 50 mL of PVA aqueous solution (0.25% w/v) containing 1 mL of DCM and emulsified under overhead stirring (250 rpm) for 4 min. After forming the emulsion droplets, the emulsion was quickly transferred to a rotary evaporator with the addition of PVA solution (150 mL) to solidify or harden the microcapsules. The microcapsules produced were centrifuged, rinsed with DI water, lyophilized and stored in a desiccator. FIG. 2A shows a SEM micrograph of a cross-sectional view of a typical microcapsule where smaller particles were successfully encapsulated within the hollow cavity or core while FIG. 2B shows a close-up view of FIG. 2A.

Figure 3:
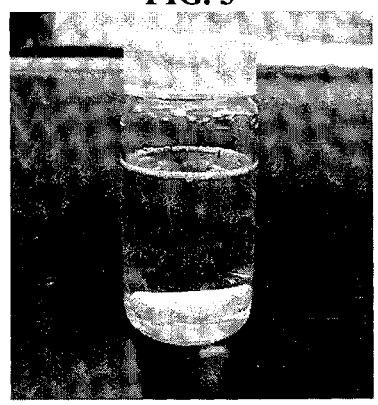
FIG. 3 shows a photograph showing all present microcapsules remained afloat after 24 h.
Figure 4:
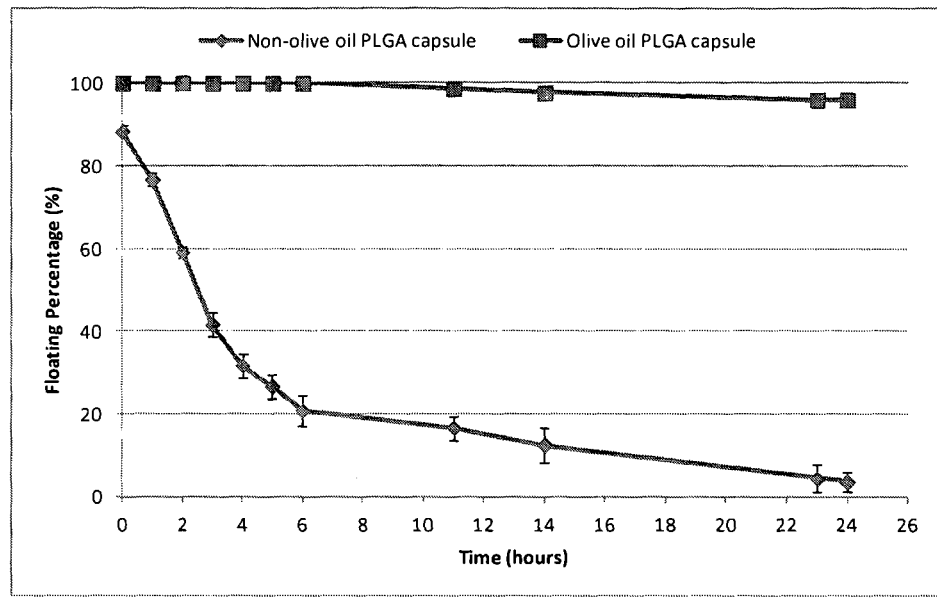
FIG. 4 is a chart showing the percent buoyancy versus time profiles of the present floating formulation compared to the non-oil-loaded microcapsules.

The buoyancy of the microcapsules was tested by visual inspection. The samples were considered buoyant only if all microcapsules remained afloat after the prescribed test time in simulated gastric fluid (SGF) (at pH 1) at 37° C. under constant agitation of 250 rpm with a magnetic stirrer. All microcapsules stayed afloat for a 24 h test cycle (FIG. 3). The olive oil-containing microcapsules fabricated using the present invention exhibited excellent floatability, as shown in FIG. 4. This floating property is due to the low density provided by hollow cavities and the hydrophobic nature of capsule shell with vegetable oil inclusion.

Figure 5:
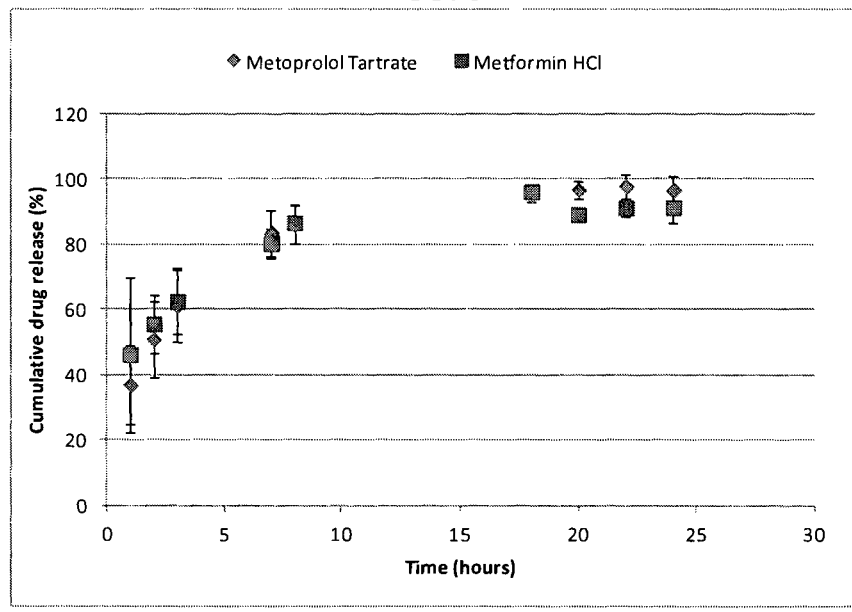
FIG. 5 shows the cumulative release profile of two different drugs (i.e. metoprolol tartrate and metformin HCl) from particles encapsulated within the present floating capsules. It is to be noted that the encapsulated particles in microcapsules had been derived from microcapsules that hosted both types of drug-loaded particles at the same time.

The drug release profile (FIG. 5) shows the simultaneous release of two drugs (i.e. metoprolol tartrate and metformin HCl) from floating microcapsules that hosted both types of drug-loaded particles over a sustained period (up to ~18 h) in SGF at 37° C.

Figure 6A:
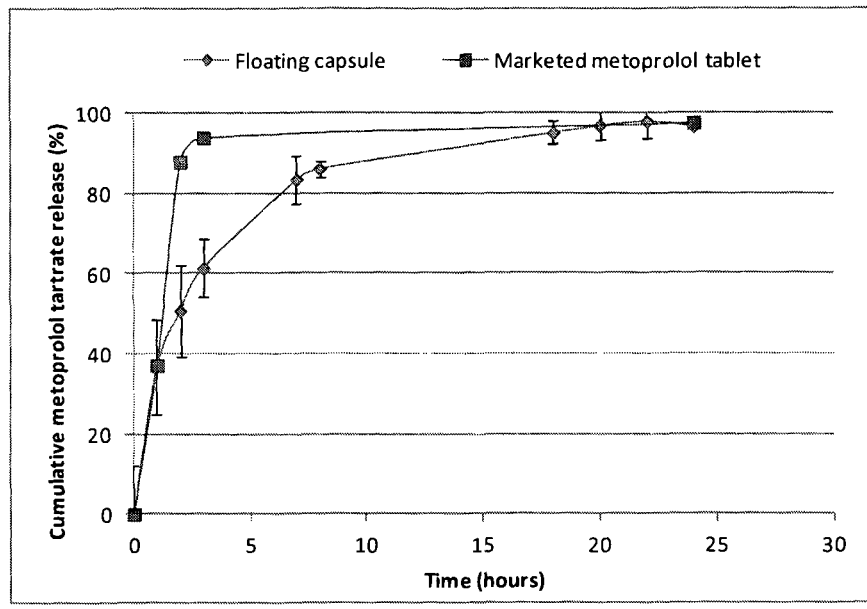
FIG. 6A shows the cumulative release profile of metoprolol tartrate from particles encapsulated within the present floating capsules and of marketed tablet. It is to be noted that the encapsulated particles in microcapsules had been derived from microcapsules that hosted both types of drug-loaded particles at the same time.
Figure 6B:
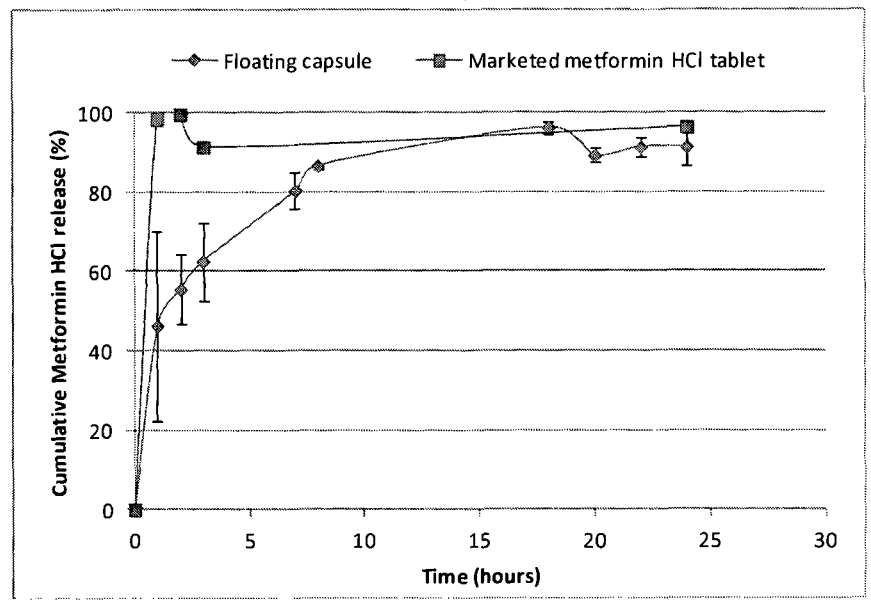
FIG. 6B shows the cumulative release profile of metformin HCl from particles encapsulated within the present floating capsules and of marketed tablet. It is to be noted that the encapsulated particles in microcapsules had been derived from microcapsules that hosted both types of drug-loaded particles at the same time.

FIGS. 6A and 6B show a more controlled and sustained release from the present floating microcapsules in comparison to the respective marketed tablets.

Example 2

Experimental Section

Materials:
Poly(DL-lactide-co-glycolide) 53/47 (PLGA 53/47, intrinsic viscosity (IV): 1.03, Purac), poly(DL-lactide-co-glycolide) 75/25 (PLGA 75/25, IV: 0.93, Purac), poly(L-lactide) (PLLA, IV: 2.38, Bio Invigor), poly(caprolactone) (PCL, molecular weight (MW): 10 kDa, Aldrich) and poly(vinyl alcohol) (PVA, MW: 30-70 kDa, Sigma-Aldrich) were used without further purification. Drugs (i.e. metoprolol tartrate salt, metformin HCl, fenofibrate), Cremophor® EL, Span 80 and n-hexane were purchased from Sigma-Aldrich. Dichloromethane (DCM), tetrahydrofuran (THF) and acetonitrile, (ACN) were purchased from Tedia Company Inc. Olive oil (Pietro Coricelli) were purchased. Phosphate-buffered saline (PBS) at pH 7.4 was from OHME, Singapore. All drugs and solvents were used as received, unless otherwise noted. The marketed tablets used were metoprolol tartrate (Lopressor®), metformin HCl (from East Pharmaceutical) and fenofibrate (Lipanthyl®). The simulated gastric fluid (SGF) (pH 1) was prepared by adding 0.1 M HCl solution (Merck) and 0.02% (w/v) Tween 20 (Tokyo Kasei). The simulated intestinal fluid (SIF) contained pH 6.8 phosphate buffer and 0.5% (w/v) Tween 80 (Sigma-Aldrich).

Fabrication of Drug-Loaded Microparticles:
For the fabrication of fenofibrate-loaded PCL particles, fenofibrate (60 mg, 30% w/w) was first added to the polymer solution (7% w/v, 0.2 g of PCL dissolved in 2.85 mL of DCM) and the resultant solution was subsequently emulsified in 50 mL PVA aqueous solution (4% w/v) under overhead stirring at 2,000 rpm for 4 min. The emulsion was then transferred quickly to rotary evaporator at room temperature (25° C.) for solvent evaporation. The hardened particles were centrifuged, rinsed with deionized water and lyophilized. Finally, free fenofibrate were washed away with n-hexane and the particles were dried in vacuum oven.

The metoprolol tartrate-loaded PLGA 75/25 particles were fabricated using Buchi Mini Spray Dryer B-290 with a 2-fluid nozzle of size. A concentration of 2% (w/v) of PLGA 75/25 was dissolved in chloroform along with metoprolol tartrate (30% w/w). Inlet temperature was set to 50° C. at a feed rate of 2.5 mL/min, and an aspirator rate of 100%. The particles were collected from the collection vessel and lower part of the cyclone. After which, the particles were reconstituted and suspended in 10 mL of PVA aqueous solution (4% w/v), followed by centrifugation, decantation and freeze-drying.

Encapsulation of Drug-Loaded Microparticles in Microcapsule:

For the encapsulation step, the pre-fabricated particles (0.09 g of fenofibrate-loaded particles and 0.07 g of metoprolol tartrate-loaded particles) were first suspended in 1 mL of PVA aqueous solution (0.1% w/v) containing 0.1 g of metformin HCl (or specified otherwise in the text). The particles/water suspension was then introduced dropwise into the PLGA solution (5% w/v, 0.3 g of PLGA 53/47 dissolved in 6 mL of DCM), followed by the addition of olive oil (0.01 mL) under magnetic stirring. The resultant mixture was added to 50 mL of PVA aqueous solution (0.25% w/v) containing 1 mL of DCM and emulsified under overhead stirring (250 rpm) for 4 min at room temperature (25° C.). After forming the emulsion droplets, the emulsion was quickly transferred to rotary evaporator with the addition of PVA solution (150 mL) to solidify the microcapsules. The microcapsules produced were centrifuged, rinsed with deionized water, lyophilized and stored in a desiccator. PLLA and PLLA-PCL (75 wt %:25 wt %) microcapsules were similarly prepared.

For comparison with the modified encapsulation method as described above, a reference microcapsule (capsule R) loaded with particles (without the addition of 0.1 g free metformin HCl) was fabricated through a conventional method in which a higher amount of PVA solution (250 mL, without DCM) was used during emulsification and no rotary evaporator was employed to harden the capsules.

Morphological Analysis:

The exterior and internal morphologies of the microparticles and microcapsules were viewed under scanning electron microscopy (SEM, JEOL JSM-6360A) at 5 kV. Prior to analysis, samples were first mounted onto a metal stub and cross-sectioned approximately at the centre line using a razor blade. Samples were then coated with gold using a sputter coater (SPI-Module). Measurement of particle/capsule size (in diameter) was performed on the SEM images using the ImageJ software.

Determination of Actual Drug Loading:

For the determination of actual loading of water-soluble metformin HCl and metoprolol tartrate, 10 mg of microparticles or microcapsules (n=3) were first dissolved in 1 mL of DCM. Extraction of the drug was then achieved with the use of 10 mL PBS. Hydrophilic metformin HCl preferentially partitions into PBS, whereas the partition coefficient of metoprolol tartrate between DCM and PBS was determined experimentally by preparing a series of concentrations and was found to be about 2. The drug content in aqueous solution was analyzed using UV-Vis spectrophotometer (Shimadzu UV-250), at the wavelength of 233 nm and 274 nm for metformin HCl and metoprolol tartrate, respectively. For the determination of highly hydrophobic fenofibrate loading, after dissolution of microparticles or microcapsules, 5 mL n-hexane was added to precipitate polymers and other drugs (if any). The mixture was centrifuged and the supernatant was dried. A 10 mL volume of SGF containing 2% w/v Cremophor EL was then added to dissolve the solid fenofibrate for UV-Vis analysis at 292 nm.

In Vitro Buoyancy Test:

The buoyancy of the microcapsules was tested through a visual observation method. For each sample of microcapsules, 50 individual microcapsules, in triplicate, were placed into 20 mL SGF filled in the vials (20 mL volume capped bottle). The test bottles were incubated in a water bath at 37° C. under magnetic stirring at 250 rpm for 24 h. At each predetermined time, the number of floating microcapsules was counted visually. The percentage of floating microcapsules (an indication of buoyancy) was calculated according to the ratio of the number of floating microcapsules to the total number of microcapsules.

Drug Release Study:

The in vitro metformin HCl and metoprolol tartrate release studies were carried out in SGF and SIF. For poorly water-soluble fenofibrate, the release test was conducted in the medium with the addition of 2% w/v Cremophor EL to maintain a sink condition. Samples (20 mg) were placed, in triplicate, in vials containing 20 mL dissolution medium and were maintained at 37° C. with a magnetic rotation speed of 250 mm. At prescribed time intervals, 1 mL of medium from each vial was removed and replaced with fresh medium. The drug content was analyzed using UV-Vis spectrophotometer ($\lambda_{metformin\ HCl}$=233 nm, $\lambda_{metoprolol\ tartrate}$=274 nm, $\lambda_{fenofibrate}$=292 nm).

Statistical Analysis:

Data from different sets of samples were compared by unpaired Student's t-test and the one-way ANOVA analysis coupled with Tukey's multiple comparison tests. Differences were considered statistically significant when $P \leq 0.05$.

Results and Discussion

Figure 7A:
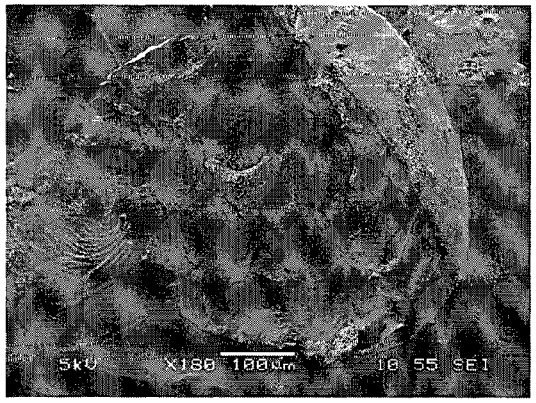
FIG. 7A shows a SEM image of cross-sectional view of a reference microcapsule (capsule R). It was found that the encapsulated particles were agglomerated and embedded within the capsule shell.
Figure 7B:
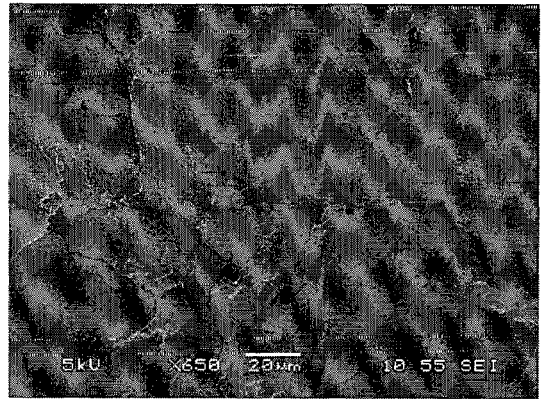
FIG. 7B shows a SEM image of close-up view of a reference microcapsule (capsule R). It was found that the encapsulated particles were agglomerated and embedded within the capsule shell.

The addition of olive oil to the shell of the microcapsule while achieving the ability to load drug-loaded particles together into the hollow cavity of the microcapsule is certainly not trivial. The inclusion of olive oil would unsettle the original formulation, leading to a change in capsule structure, morphology, encapsulation capability of the microcapsule, and particle localization within the microcapsule. To verify this point, a reference set of microcapsules (capsule R) with the inclusion of olive oil (a non-solvent for capsule polymer) was fabricated through a conventional method. In this conventional method, a higher amount of PVA solution (without DCM) was used during emulsification and no rotary evaporator was employed to harden the capsules. The cross-sectional and close-up views (FIGS. 7A and 7B) of the microcapsules (capsule R) reveal that the encapsulated particles were agglomerated and embedded within the capsule shell. This is believed to be caused by a change in the solvent quality of the oil phase (i.e. poly(D,L-lactide-co-glycolide, 53/47) (PLGA 53/47) capsule polymer, DCM and olive oil), and the subsequent formation of an adhesive gel layer at the inner water-oil interface. As PLGA is insoluble in olive oil, the solvent quality of the oil phase is reduced and PLGA is not completely solubilized during DCM extraction and evaporation. On the other hand, the surface activity of PLGA has been demonstrated by the fact that PLGA reduces the interfacial energy between the water and oil phases. As such, the W/O/W emulsion is in a kinetically stable state due to the absorption of PLGA molecules to the inner and outer water-oil interfaces and the presence of PVA as a surfactant at the water-oil interface. As the solvent quality decreased, PLGA molecular chains at the interface would form an adhesive gel layer, which has been similarly reported in copolymer-stabilized double emulsions. Encapsulated particles within the inner water phase subsequently adhered to this gel layer, resulting in the localization of agglomerated particles within the shell of the microcapsule. The embedment of drug-loaded particles within the shell would cause the formation of pores in the shell matrix upon drug release, which would then decrease the buoyancy as a result of higher water ingress. In addition, hydrophilic drug-loaded particles embedded within the shell of the capsule would promote water influx and decrease the buoyancy.

Figure 8A:
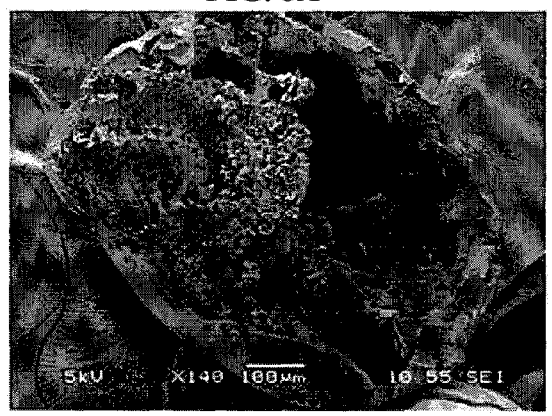
FIG. 8A shows a SEM image of a cross-sectional view of the present microcapsule where smaller particles were encapsulated within the hollow cavity.
Figure 8B:
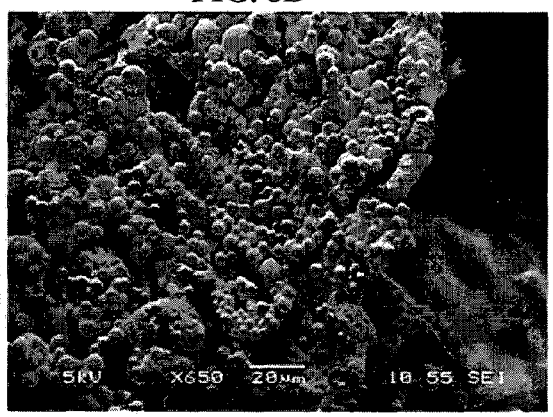
FIG. 8B shows a SEM image of a close-up view of the present microcapsule where smaller particles were encapsulated within the hollow cavity.
Figure 9:
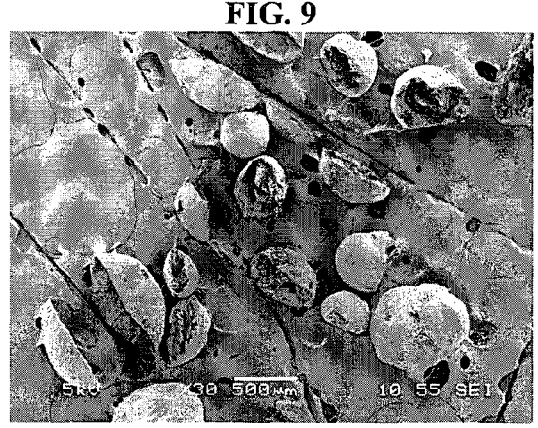
FIG. 9 shows a SEM image of cross-sectional view of many olive-oil containing microcapsules demonstrating homogeneity of the present capsule morphology.

Tweaking some process parameters therefore allows for the successful fabrication of olive oil-containing microcapsules, as evidenced from the scanning electron microscopy (SEM) (FIGS. 8A and 8B). The size of the microcapsule was 621±91 mm. Close-up examination of cross-sectioned microcapsules showed many smaller particles (6.8±2.2 mm) on the interior walls of the microcapsules. The formation efficiency of this capsule structure was estimated to be at ~100% (FIG. 9). In order to encapsulate the drug-loaded particles within the hollow cavities of the floating capsules, diffusional mass transport processes of solvent molecules have to be manipulated. DCM diffuses into the continuous aqueous phase before evaporating at the water-air interface during the solvent removal process. The solubility of DCM in water is about 1-2% v/v, therefore, increasing the oil-to-water ratio and saturating the continuous aqueous phase with DCM during the emulsification step would result in a decrease in the solvent extraction rate. This would reduce the probability of the formation of an adhesive gel layer as the solvent quality remains unchanged. Subsequently, during the hardening process, the solvent removal rate can be accelerated through the use of a rotary evaporator under reduced pressure, and with the addition of extra water. As a result, an increased removal rate of DCM from the emulsion droplets to the external aqueous phase reduces the time allowed for the adhesion process between the encapsulated particles and inner water-oil interface to take place. This would give rise to a true encapsulation of particles within the microcapsule, instead of the embedment of these particles within the microcapsule shell.

Figure 10:
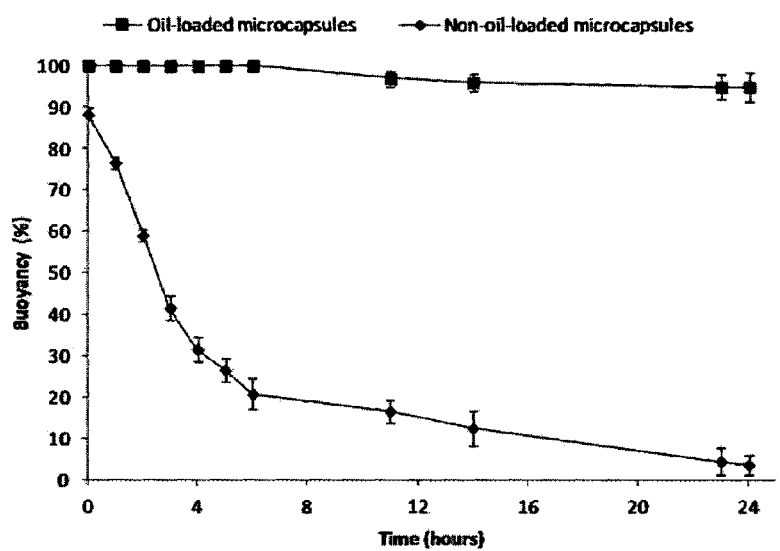
FIG. 10 shows a chart of percent buoyancy versus time profiles of the present floating formulation compared with the non-oil-loaded microcapsules.
Figure 11:
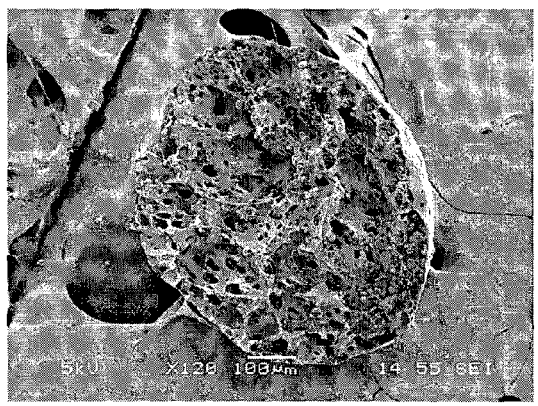
FIG. 11 shows a SEM image of cross-sectional view of a non-oil-loaded microcapsule, whereby particles were located within the hollow cavity.
Figure 12A:
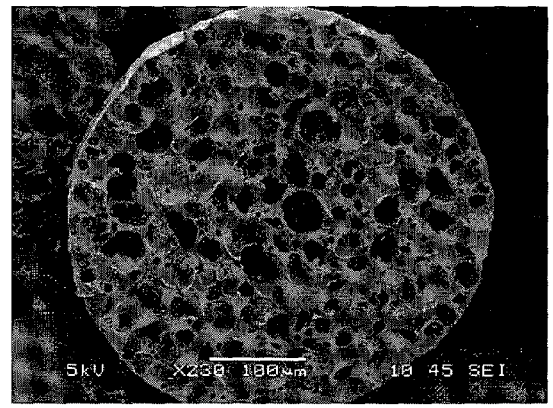
FIG. 12A shows a SEM image of a cross-sectional view of an oil-loaded microcapsule with honeycomb structure.
Figure 12B:
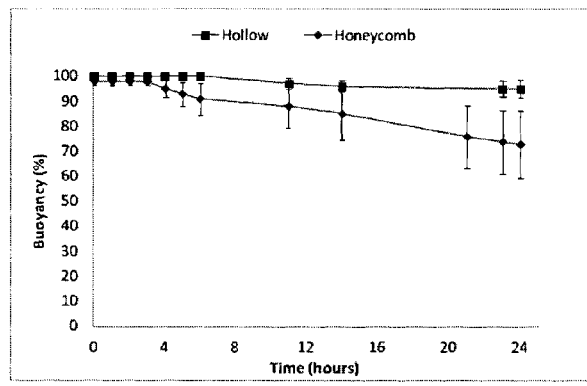
FIG. 12B shows a chart of percent buoyancy versus time profiles of the present floating formulation with hollow structure compared to the honeycomb-structured microcapsules (oil-loaded) of FIG. 12A. Higher density due to the decrease in cavity volume, as a result of honeycomb structure, reduced the buoyancy.
Figure 13A:
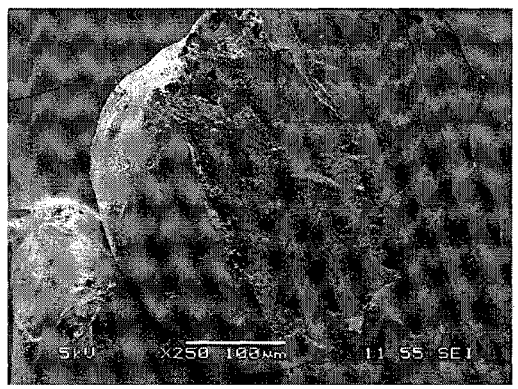
FIG. 13A shows a SEM image of a cross-sectional view of an oil-loaded microcapsule of size 224±53 μm.
Figure 13C:
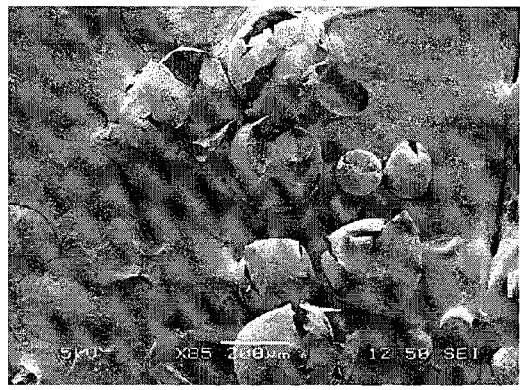
FIG. 13C shows a SEM image of cracked microcapsules after 24 h in vitro.
Figure 13B:
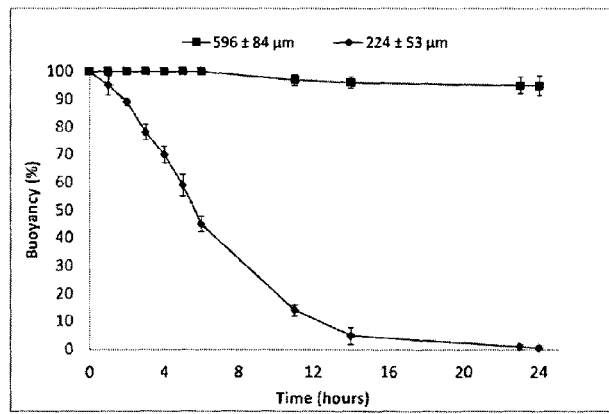
FIG. 13B shows a chart of percent buoyancy vs time profiles of the present floating formulation (596±84 μm) compared with the smaller-sized microcapsules (224±53 μm).

To mimic the in vivo gastric residence behavior, the floating ability of the microcapsules was investigated in simulated gastric fluid (SGF) at 37° C. under magnetic stirring at 250 rpm for 24 h. The buoyancy profiles are shown in FIG. 10. Olive oil-containing microcapsules (596±84 mm) were able to float continuously for over 24 h, while almost all the non-oil-loaded microcapsules (618±93 mm) (refer to FIG. 11 for morphological analysis) sank. In contrast to the conventional gas-generating floating devices, these oil-loaded microcapsules floated immediately upon contact with the SGF, without any lag time in buoyancy. This excellent floating property could be due to the combined effects of the capsule's low density provided by both the hollow cavity (FIGS. 12A and 12B) and the hydrophobic nature (i.e. reduced medium uptake) of the capsule shell with olive oil. It was found that larger microcapsules (596±84 mm) allowed for better floatability as the buoyancy decreased with decreasing capsule size due to reduced cavity volume. Also, it was observed that cracks on the surface of smaller capsules (224±53 mm) would further decrease their buoyancy (FIGS. 13A, 13B and 13C). In addition, it was also noted that drug incorporation and subsequent release of drugs did not impair the buoyancy of the microcapsules.

Figure 14A:
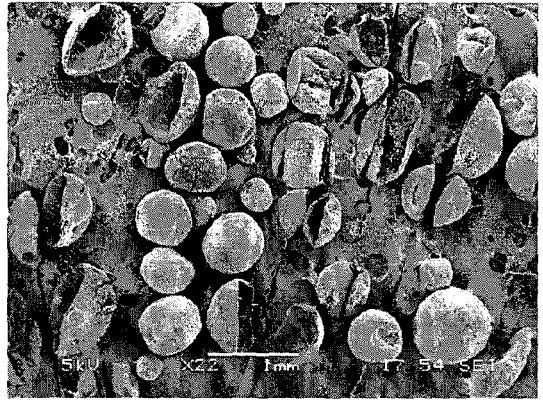
FIG. 14A shows a SEM image of a cross-sectional view of the microcapsules, whereby the drug-loaded particles and free metformin HCl were attached onto the inner wall of the microcapsule.
Figure 14B:
FIG. 14B shows a SEM image of a close-up view of a microcapsule (×120), whereby the drug-loaded particles and free metformin HCl were attached onto the inner wall of the microcapsule.
Figure 14C:
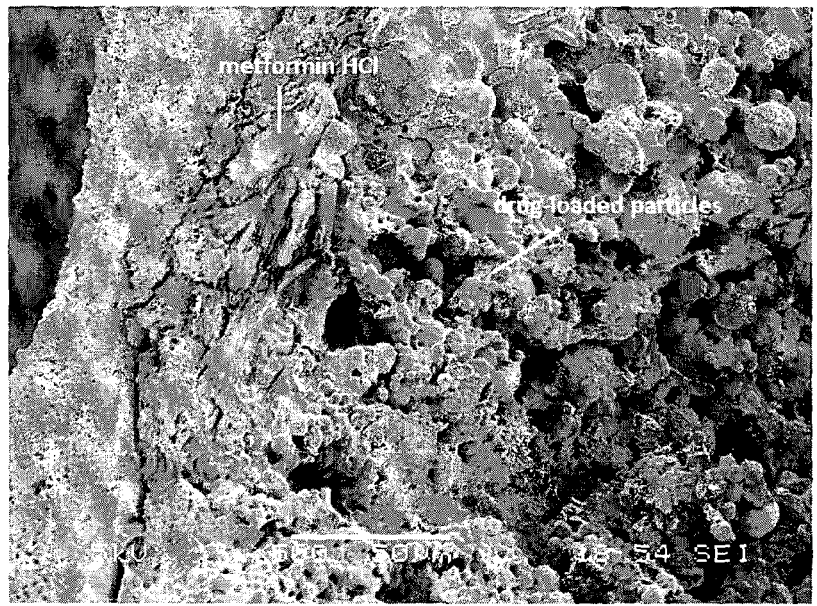
FIG. 14C shows a SEM image of a close-up view of a microcapsule (×500) of FIG. 14B, whereby the drug-loaded particles and free metformin HCl were attached onto the inner wall of the microcapsule.

Metoprolol tartrate-loaded PLGA 75/25 particles (4.9±1.8 mm) and fenofibrate-loaded PCL particles (9.7±3.8 mm) together with free metformin HCl were encapsulated into the microcapsules (596±84 mm) for the drug release study conducted in SGF medium. Comparable sizes were also observed for the other microcapsule groups. Hydrophilic metformin HCl can be easily dissolved in water, and thus allowed for direct encapsulation into the microcapsule. The SEM image (FIG. 14) shows similar results whereby the drug-loaded particles and free metformin HCl were found to be encapsulated within the hollow cavities of the microcapsules. For the microcapsules, the actual loading of metoprolol tartrate, fenofibrate and metformin HCl were 0.82±0.02 wt %, 1.89±0.03 wt %, 10.92±0.16 wt %, respectively. The amount of each loaded drug in the floating microcapsules (800 mg) was determined at a dose of approximately 10% equivalent to marketed formulations, i.e. 5 mg for metoprolol tartrate, 20 mg for fenofibrate and 50 mg for metformin HCl. It is noted that delivery devices with prolonged GRT would increase the bioavailability of drugs, thus requiring a lower dosage. Furthermore, when used for preventive measures, dosages are relatively lower compared to therapeutic applications.

Figure 15A:
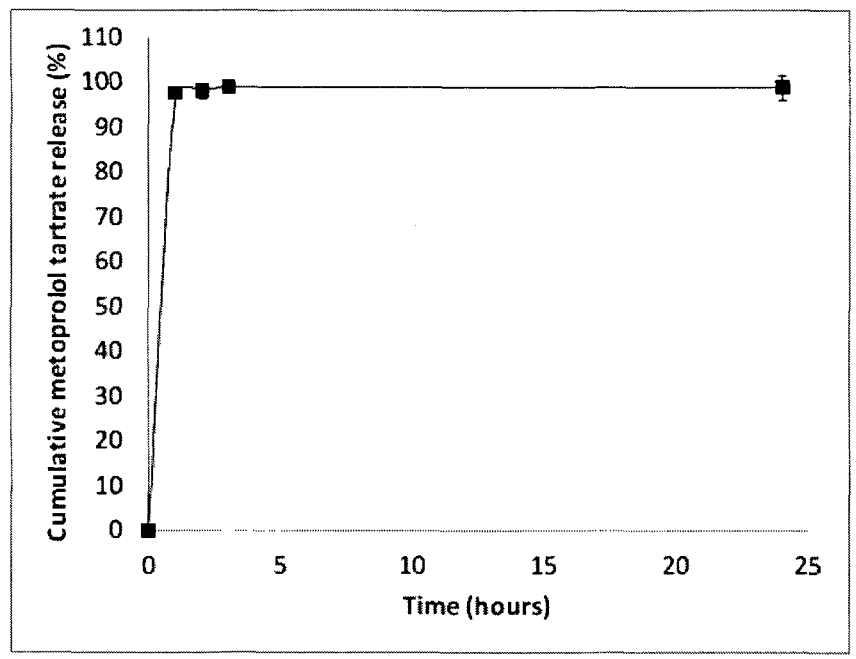
FIG. 15A shows release profiles of metoprolol tartrate from PLGA 75/25 particles.
Figure 15B:
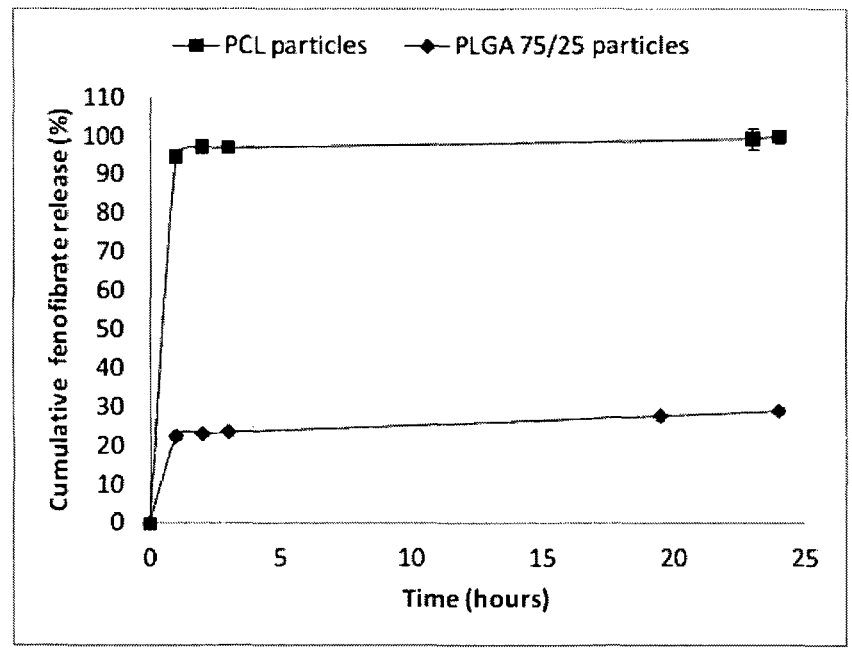
FIG. 15B shows release profiles of fenofibrate from PCL and PLGA 75/25 particles.

The polymer type of the drug-loaded particles was selected such that 100% release from free particles was obtained within 1 h in SGF at 37° C. When these particles are encapsulated within the hollow cavities of the microcapsules, it is hypothesized that the shell of the microcapsule would serve as an additional diffusion barrier, thus limiting initial burst and controlling release rates. It was observed that PLGA 75/25 particles alone exhibited nearly 100% metoprolol tartrate release within 1 h (FIG. 15A). The fast release could be due to the high drug loading (~25% w/w) and the high aqueous solubility of the drug, which caused a huge burst release from the PLGA particles upon SGF ingress. On the other hand, there was 100% release of fenofibrate from poly(caprolactone) (PCL) particles within 1 h, whereas fenofibrate release from PLGA 75/25 particles proceeded relatively slower (cumulative release of 25% for 24 h) (FIG. 15B). The more rapid release of hydrophobic fenofibrate from PCL particles could be due to the highly flexible rubbery state of PCL with a glass transition temperature of –60° C. At the drug release condition of 37° C. and surrounded by SGF, PCL chains are in a highly mobile state with increased free volume, which allows for better dissolution of the hydrophobic drug and promotes further release.

Figure 16A:
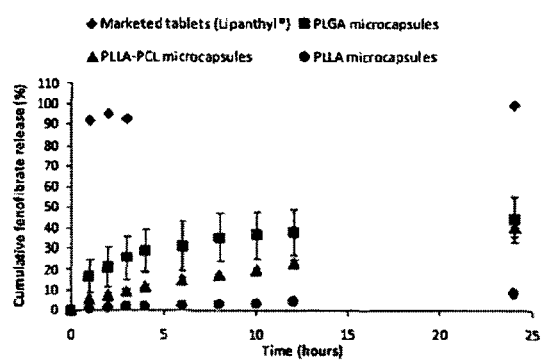
FIG. 16A shows release profiles of fenofibrate from various floating microcapsule groups and marketed tablets in SGF. It should be noted that the release profile of each drug from microcapsules had been derived from the microcapsules that co-encapsulated three different drugs.
Figure 16B:
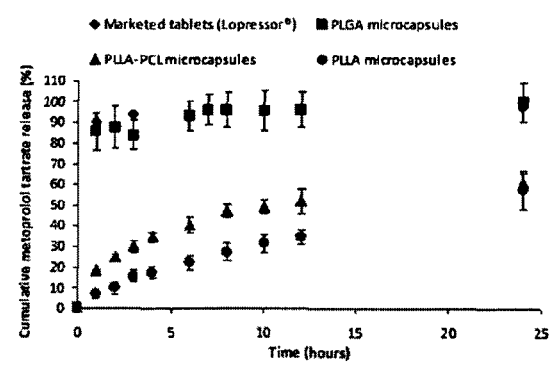
FIG. 16B shows release profiles of metoprolol tartrate salt from various floating microcapsule groups and marketed tablets in SGF. It should be noted that the release profile of each drug from microcapsules had been derived from the microcapsules that co-encapsulated three different drugs.
Figure 16C:
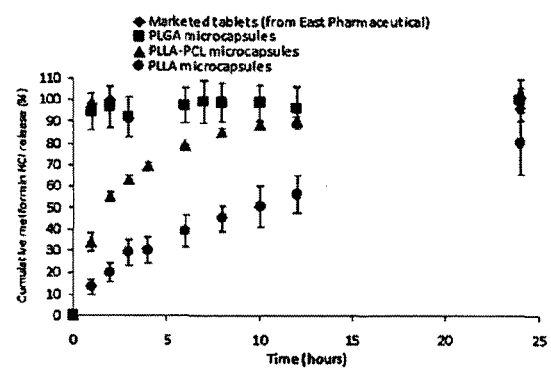
FIG. 16C shows release profiles of metformin HCl from various floating microcapsule groups and marketed tablets in SGF. It should be noted that the release profile of each drug from microcapsules had been derived from the microcapsules that co-encapsulated three different drugs.

The drug-loaded particles, in their respective polymer types, were now encapsulated within the microcapsules. The release profiles of fenofibrate (log P=5.2, highly hydrophobic), metoprolol tartrate salt (log P=1.6, hydrophilic) and metformin HCl (log P=–2.64, highly hydrophilic) from non-floating marketed tablets and floating microcapsules of various shell polymer types are shown in FIGS. 16A-16D. From the release studies, each marketed tablet exhibited relatively rapid drug release, while the microcapsules provided a more controlled release. The suppression of release from microcapsules was highly evident for fenofibrate (FIG. 16A). It is noted that the dissolution process of fenofibrate occurs with great difficulty due to its neutral and lipophilic nature. This fact highlights the importance of a substantial amount of SGF uptake required for fenofibrate release. The marketed fenofibrate tablets (capsule) (Lipanthyl®) allowed for direct access of drug powder to SGF after the rapid dissolution of the gelatin shell, thus leading to a huge burst release upon quick SGF influx. The shell of the microcapsule, on the other hand, would limit the rate of SGF influx, and serve as a rate-limiting layer that impedes rapid drug loss and controls drug diffusion rates. However, for the release of metoprolol tartrate and metformin HCl from PLGA 53/47 microcapsules (FIGS. 16B and 16C), the retardation of release by the PLGA shell was observed to be insignificant. This result could be due to the fact that the relatively hydrophilic PLGA 53/47, arising from its fully amorphous structure, is permeable to water-soluble molecules. As such, metoprolol tartrate and metformin HCl drug molecules diffused rapidly through PLGA. Changing the polymer type of the capsule's shell had an effect on drug release kinetics (FIGS. 16A-16C). It is clear that the semicrystalline morphology and relatively hydrophobic nature of the PLLA shell retard appreciable medium influx and limits drug diffusion, thus giving rise to the slowest drug release rates. In contrast to the pure PLLA shell, the incorporation of PCL nanoparticulates (25 wt %) into the PLLA shell (FIG. 17) was found to accelerate the drug release and to result in a more consistent release (FIGS. 16A-16D), which would be advantageous in achieving sustained release. The PLLA-PCL shell was less dense due to the presence of rubbery PCL, which resulted in a relatively faster release.

Figure 16D:
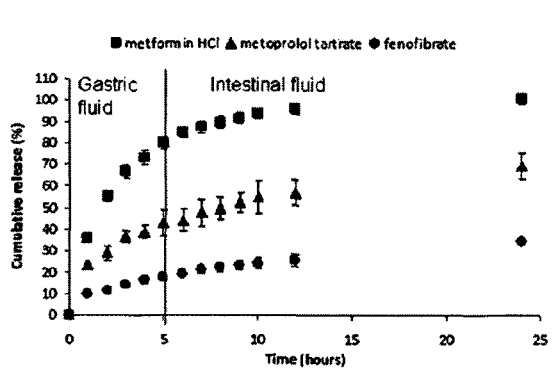
FIG. 16D shows release profiles of three different drugs (i.e. fenofibrate, metoprolol tartrate salt and metformin HCl) from a single PLLA-PCL microcapsule in SGF for 5 h followed by release into SIF at 37° C. It should be noted that the release profile of each drug from microcapsules had been derived from the microcapsules that co-encapsulated three different drugs.
Figure 17:
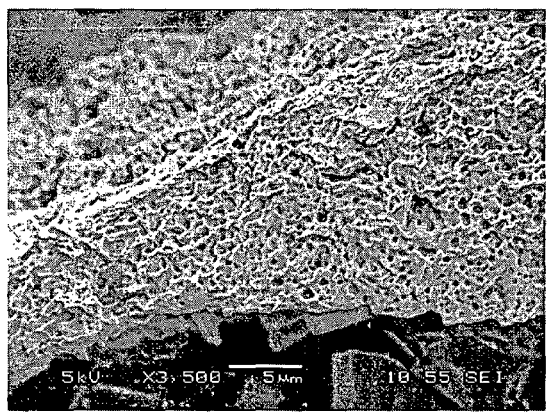
FIG. 17 shows a SEM image of cross-sectional view of PLLA capsule shell containing PCL nanoparticulates after dissolution with THF. The dissolution test is based on the solubility differences of the polymers in THF (i.e. PCL is soluble in THF; PLLA is not). After THF dissolution, only the PLLA shell remained; the nanopores were identified as PCL.
Figure 18A:
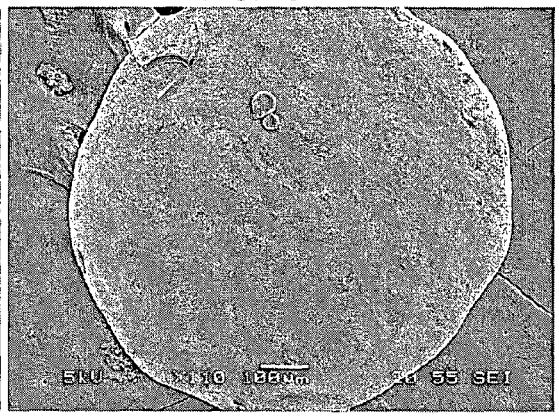
FIG. 18A shows a SEM image of a surface view of the present microcapsules after 24 h in vitro.
Figure 18B:
FIG. 18B shows a SEM image of a cross-sectional view of the present microcapsules after 24 h in vitro.
Figure 18C:
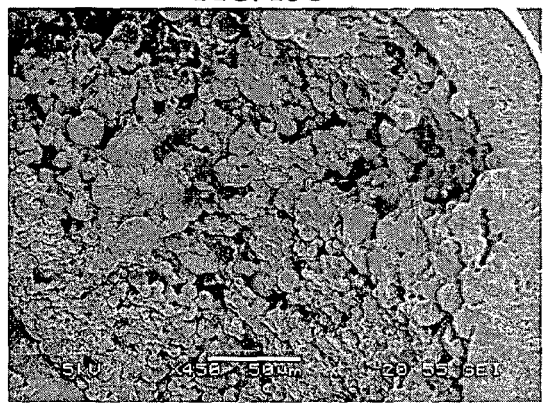
FIG. 18C shows a SEM image of a close-up view of the present microcapsules after 24 h in vitro.

The drug release profiles of three different drugs from a single PLLA-PCL microcapsule for 5 h in SGF (pH 1) followed by release in simulated intestinal fluid (SIF, pH 6.8) at 37° C. are shown in FIG. 16D. Multiple drugs, each with a different hydrophilicity, were observed to be released from the microcapsules in a sustained manner for 24 h. It has been reported that floating microspheres can exhibit prolonged GRT of 5 h in humans. The release data demonstrate that certain amounts of drugs would be released in the stomach depending on the gastric emptying time and the remaining incorporated drugs would be released in the intestinal region, as similarly reported by other groups. The release of metformin HCl was observed to be the fastest. This could be explained by the fact that the highly hydrophilic drug was encapsulated into the capsule in the form of free drug, while the encapsulation of fenofibrate and metoprolol tatrate within the particles was deemed to further control the release kinetics. For the release from drug-loaded particles within microcapsules, metoprolol tartrate was released more rapidly as a result of its highly water-soluble nature, which facilitates drug dissolution, in comparison with the fenofibrate release. Surface and cross-sectional views of microcapsules (FIG. 18) show that the capsule shell and encapsulated particles still remained intact after 24 h in vitro, suggesting diffusional drug release. In addition, the absence of metformin HCl free drug was observed within the cavities of the microcapsules after 24 h, which concurs with its complete release. The main absorption site of metformin HCl was reported to be the proximal small intestine. Thus, its substantial release from a gastroretentive system in the upper GI tract (5-7 h) would clearly be advantageous. On the other hand, although a relatively slow release was observed for fenofibrate and metoprolol tartrate within the first 5 h (in gastric fluid), the remaining drugs after gastric emptying process would still be absorbed throughout the intestinal tract. For a drug with low release rate (usually for hydrophobic drugs) or high dosage demand, microcapsules given along with a small loading dose (free drug) would provide a higher plasma drug concentration over a prolonged period. It is also worth mentioning that the integrity of the shell of microcapsules exiting the stomach may be impaired, which would then accelerate the drug release in the intestinal fluid.

In conclusion, the microencapsulation of drug-loaded particles within the hollow cavity of a floating polymer-based microcapsule through a modified emulsion solvent evaporation method was demonstrated. Simply by designing and tailoring the delivery system, multiple drugs can be loaded, and their release profiles can be fine-tuned accordingly. As a result, this system may be a promising platform to deliver multiple drugs orally, while providing controlled and sustained release.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method for forming a floating capsule encapsulating particles (S) loaded with one or more drugs, comprising:
suspending the particles (S) in an aqueous phase (W1) to form a S/W1 phase;
contacting the S/W1 phase with a solution of a polymer (O) in a first organic solvent to form a S/W1/O phase;
adding a water-immiscible oil with a density lower than water to the S/W1/O phase;
combining the S/W1/O phase including the water-immiscible oil with a water bath (W2) comprising a surfactant and a second organic solvent and emulsifying the resulting mixture to form a S/W1/O/W2 phase; and
evaporating under reduced pressure the organic solvents in the S/W1/O/W2 phase to obtain the capsule.

2. The method of claim 1, wherein the water-immiscible oil is a vegetable oil, wherein the vegetable oil:first organic solvent volume ratio is 1% or less.

3. The method of claim 2, wherein the vegetable oil:first organic solvent volume ratio is 0.5% or less.

4. The method of claim 3, wherein the vegetable oil:first organic solvent volume ratio is 0.2% or less.

5. The method of claim 1, wherein the water bath (W2) contains a saturated amount of the second organic solvent.

6. The method of claim 1, wherein the S/W1/O/W2 phase comprises a polymer solution:water bath (O/W2) ratio of 12% v/v or more.

7. The method of claim 1, wherein evaporating the organic solvent under reduced pressure further comprises adding more water or surfactant to the S/W1/O/W2 phase.

8. The method of claim 1, further comprising filtering, rinsing, lyophilizing or storing the capsule.

9. The method of claim 1, wherein the water-immiscible oil is olive oil.

10. The method of claim 1, wherein the first and second organic solvent which are immiscible with water are independently selected from the group consisting of dichloromethane (DCM), ethyl acetate (EAc), methyl ethyl ketone (MEK), tetrahydrofuran (THF), chloroform, pentane, benzene, benzyl alcohol, and carbon tetrachloride.

11. The method of claim 10, wherein the first and second organic solvents are the same.

12. The method of claim 1, wherein the surfactant is selected from the group consisting of polyvinyl alcohol (PVA), sodium dodecyl sulfate (SDS), sodium pentane sulfonate, dehydrocholic acid, glycolithocholic acid ethyl ester, ammonium lauryl sulfate and other alkyl sulfate salts, sodium laureth sulfate, alkyl benzene sulfonate, soaps, fatty acid salts, poloaxamers, alkyl poly(ethylene oxide), diethylene glycol monohexyl ether, copolymers of poly(ethylene oxide) and poly(propylene oxide), hexaethylene glycol monohexadecyl ether, alkyl polyglucosides, digitonin, ethylene glycol monodecyl ether, cocamide MEA, cocamide DEA, cocamide TEA, fatty alcohols, cetyl trimethylammonium bromide (CTAB), dodecylethyldimethylammonium bromide (D12EDMAB), didodecyl ammonium bromide (DMAB), cetylpyridinium chloride (CPC), polyethoxylated tallow amine (POEA), hexadecyltrimethylammonium p-toluenesulfonate, benzalkonium chloride (BAC), benzethonium chloride (BZT), dodecyl betaine, sodium 2,3-dimercaptopropanesulfonate monohydrate, dodecyl dimethylamine oxide, cocamidopropyl betaine, 3-[N,N-dimethyl(3-palmitoylaminopropyl)ammonio]-propanesulfonate, coco ampho glycinate, and mixture thereof.

13. The method of claim 12, wherein the surfactant is PVA.

14. The method of claim 1, wherein the polymer solution (O) contains an water-insoluble polymer selected from the group consisting of poly(lactide) (PLA), poly(glycolide) (PGA), poly(ε-caprolactone) (PCL), poly(δ-valerolactone), poly(γ-butyrolactone), poly(trimethylene carbonate), polyisopropylacrylamide, poly(hydroxylbutyrate-co-hydroxyvalerate) (PHB or PHBV) and a copolymer or mixture thereof.

15. The method of claim 14, wherein the polymer is poly (L,D-lactic-co-glycolic acid) (PLGA).

16. The method of claim 1, wherein the particles (S) comprise one or more types of particles, each type of particle loaded with a different drug or drug combination.

17. The method of claim 1, wherein the one or more drugs are selected from the group consisting of ibuprofen (IBU), metoclopramide HCl (MCA) lidocaine, atorvastatin, clopidogrel, enoxaparin, celecoxib, omeprazole, esomeprazole, fexofenadine, quetiapine, metoprolol tartrate, metformin hydrochloride, fenofibrate, budesonide, and a mixture thereof.

18. A floating capsule formed of a core-shell structure, prepared according to the method of claim 1, wherein particles loaded with one or more drugs are encapsulated within the core and the shell is free of the particles.

19. The floating capsule of claim 18, wherein the capsule is a sustained release or controlled release capsule.

20. A method for delivering one or more drugs to the gastrointestinal tract, comprising the oral administration of a floating capsule according to claim 18.

* * * * *